(12) United States Patent  
Kang et al.

(10) Patent No.: US 9,508,525 B2  
(45) Date of Patent: Nov. 29, 2016

(54) APPARATUS AND A METHOD FOR GENERATING A FLATTENING X-RAY RADIATION FIELD

(71) Applicants: NUCTECH COMPANY LIMITED, Haidian District Beijing (CN); Tsinghua University, Haidian District Beijing (CN)

(72) Inventors: Kejun Kang, Haidian District Beijing (CN); Chuanxiang Tang, Haidian District Beijing (CN); Huaping Tang, Huaibi (CN); Huaibi Chen, Haidian District Beijing (CN); Wenhui Huang, Haidian District Beijing (CN)

(73) Assignees: NUCTECH COMPANY LIMITED, Haidian, Beijing (CN); Tsinghua University, Haidian, Beijing (CN)

( * ) Notice: Subject to any disclaimer, the term of this patent is extended or adjusted under 35 U.S.C. 154(b) by 247 days.

(21) Appl. No.: 14/494,178

(22) Filed: Sep. 23, 2014

(65) Prior Publication Data  
US 2015/0085989 A1 Mar. 26, 2015

(30) Foreign Application Priority Data  
Sep. 23, 2013 (CN) .......................... 2013 1 0433778

(51) Int. Cl.  
*A61N 5/10* (2006.01)  
*H01J 35/14* (2006.01)  
*H01J 35/06* (2006.01)  
*H01J 35/10* (2006.01)  
*H05H 7/06* (2006.01)

(52) U.S. Cl.  
CPC ............. *H01J 35/14* (2013.01); *A61N 5/1077* (2013.01); *H01J 35/06* (2013.01); *H01J 35/106* (2013.01); *H01J 2235/068* (2013.01); *H01J 2235/086* (2013.01); *H01J 2235/1262* (2013.01); *H05H 7/06* (2013.01)

(58) Field of Classification Search  
CPC ....................................................... A61N 5/10  
See application file for complete search history.

(56) References Cited

U.S. PATENT DOCUMENTS

| 4,627,089 A | 12/1986 | Menor et al. |
| 4,726,046 A * | 2/1988 | Nunan ................. A61N 5/1042 250/492.1 |
| 8,350,226 B2 * | 1/2013 | Zdasiuk ............... A61N 5/1043 250/396 ML |
| 2008/0067449 A1 * | 3/2008 | Guertin .................... A61N 5/10 250/493.1 |
| 2009/0122961 A1 | 5/2009 | Ohsawa |

* cited by examiner

*Primary Examiner* — Thomas R Artman  
(74) *Attorney, Agent, or Firm* — Knobbe Martens Olson & Bear LLP

(57) ABSTRACT

An apparatus and a method are for generating a flattening x-ray radiation field. The apparatus includes: plurality of electron accelerators for generating high-energy electron beam current; and a common target unit including a vacuum target chamber, a target and plurality of input connectors. The plurality of input connectors are connected to one side of the vacuum target chamber and the target is installed at the other side of the vacuum target chamber opposing the plurality of input connectors, the axes of which intersect in pairs at one point in an predetermined included angle. The plurality of electron accelerators are connected to the plurality of input connectors.

20 Claims, 5 Drawing Sheets

(A)

(B)

APPARATUS AND A METHOD FOR GENERATING A FLATTENING X-RAY RADIATION FIELD

CROSS-REFERENCE TO RELATED APPLICATION

This application claims priority to Chinese Patent Application No. 201310433778.7, filed on Sep. 23, 2013, the disclosure of which including the specification, the drawings, and the claims is hereby incorporated by reference in its entirety.

TECHNICAL FIELD

The present application relates to an apparatus and a method for generating a flattening x-ray radiation field, in particular to an apparatus and a method for generating a flattening x-ray radiation field by applying the high-energy electron accelerator to the nondestructive injury detection, radiation imaging, fluoroscopic imaging, security check device, radiation processing and medical radiation therapy.

BACKGROUND

Currently, x-rays present a wide range of applications in the fields of nondestructive detection, security check and medical diagnoses and treatment etc. High-energy x-rays are required for the fluoroscopy inspection of large detection objects, e.g. boilers, aerospace engines, bulk cargos in the airport or at the customs or transported by the railway. In such cases, high-energy x-rays are generated by the electron accelerator with the energy above 2 MeV.

Generally, the basic method that the electron accelerator generates x-rays includes: generating electron beam current by an electron gun; providing the electron beam current with high energy via the acceleration by the electric field; and generating x-rays as the high-energy electron beam current bombards the target. The area where x-rays (or useful x-rays) are distributed is termed as x-rays radiation field. The x-rays generated via the bombarding by the electron beam current are distributed divergently to each orientation in 4Π solid angle. The intensity distribution of the x-rays generated via bombarding the target by the electron beam current with different energy in each transmitting direction is various. Generally, the higher the energy of the electron beam current is, the larger the intensity of the forward x-rays is. In general, the moving direction of the electron beam current is defined as forward. With regards to the intensity of the x-rays generated via bombarding the target by the high-energy electron beam current in various directions, the intensity of the x-rays generated via bombarding the target by the high-energy electron beam current in the forward direction is the biggest, and decreases as the angle deviates the forward direction increases. The higher the energy of the electron beam current is, the more obvious the change is. For example, take the x-rays generated via the bombarding by the electron beam current with the energy of 9 MeV (million electron volts) as an example, if the intensity of the x-rays in the center (forward) is 1, the intensity of the x-rays in the direction deviating the center 5 degrees is about 73%, 10 degrees about 53%, 15 degrees about 40%, 30 degrees about 18%. This is a very obvious forward concentrating distribution. In the inspection system which performs fluoroscopic imaging by the x-rays generated by the electron accelerator, the larger the volume of the objects to be inspected is, the higher the energy of the required x-rays is, and the distributed angle of the x-rays required is larger. However, the intensity distribution of the x-rays radiation field with high energy and large distributed angle is extremely nonuniform which decreases the quality of the detected image dramatically. In addition, in the aspect of medical radiation therapy, because the intensity distribution of the x-rays radiation field is nonuniform, the severe problem that the central (forward) area is radiated excessively whereas the marginal area is radiated insufficiently is occurred.

In the prior art, to eliminate the adverse effect imposed on the image quality caused by the non-uniform intensity distribution of the radiation field generated by the x-rays of forward concentration, or to eliminate the non-uniform radiation in the radiotherapy, in general, some blocking devices, termed as flattening filter, are arranged in front of the target generating the x-rays, such that the intensity of the forward x-rays within the small range weakens rendering the intensity distribution of the x-rays within a certain range of angles relative uniform. This way of doing is "Shaving high and approaching low" which sacrifices the maximum intensity of the radiation field generated by the electron accelerator resulting in the reduced utilization efficiency, the blurry target spots in a radiation fluoroscopic imaging system and a lowered image resolution.

SUMMARY

The present applicant is proposed to address the aforementioned problems, the aim of which is to provide an apparatus and a method for generating flattening x-ray radiation field.

To achieve the above objectives, the present application provides an apparatus for generating a flattening x-ray radiation field comprises: plurality of electron accelerators for generating high-energy electron beam current; and common target unit comprising vacuum target chamber, target and plurality of input connectors; wherein, the plurality of electron accelerators are connected to the plurality of input connectors.

In addition, in the apparatus generating flattening x-ray radiation field of the disclosure, the plurality of input connectors are connected to one side of the vacuum target chamber and the target is installed at the other side of the vacuum target chamber opposing the plurality of input connectors, the axes of the plurality of input connectors intersect in pairs at one point in an predetermined included angle.

In addition, in the apparatus generating flattening x-rays radiation field of the disclosure, the predetermined included angles of the axes of the plurality of input connectors intersect in pairs are same.

In addition, in the apparatus generating flattening x-rays radiation field of the disclosure, the predetermined included angles of the axes of the plurality of input connectors intersect in pairs are different.

In addition, in the apparatus generating flattening x-rays radiation field of the disclosure, the target is a flat structure and the electron beam current entering into the vacuum target chamber from the plurality of input connectors intersect at one point on the target at the vacuum side.

In addition, in the apparatus generating flattening x-rays radiation field of the disclosure, the target is a spherical structure and the electron beam currents entering into the vacuum target chamber from plurality of input connectors intersect at the center of the spherical surface.

In addition, in the apparatus generating flattening x-rays radiation field of the disclosure, the target is a structure of "L" shape and the electron beam current entering into the vacuum target chamber from the plurality of input connectors is incident on the target surface vertically.

In addition, in the apparatus generating flattening x-rays radiation field of the disclosure, the common target unit further comprises: a cooling means installed outside the vacuum target chamber enclosing one surface of the target, the interior thereof is a pipe or a cavity through which the coolant is flowable inside the cooling means so as to cool the target; a refrigeration system connected to the cooling means delivering the coolant of constant low temperature to the cooling means and decrease the temperature of the high temperature coolant flowing back from the cooling means to a predetermined value.

In addition, in the apparatus generating flattening x-rays radiation field of the disclosure, the common target unit further comprises: a vacuum system installed on the side wall of the common target unit and seal connected to the vacuum target chamber such that a high vacuum can be maintained in the vacuum target chamber during operation.

In addition, in the apparatus generating flattening x-rays radiation field of the disclosure, the common target unit further comprises: plurality of focusing means installed outside the input connecting means; a focusing control means connected to the focusing means to control the operating state of the focusing means.

In addition, in the apparatus generating flattening x-rays radiation field of the disclosure, the plurality of electron accelerators are electron linear accelerators having the same structure, wherein the electron accelerator is composed of an electron transmitting unit, an output connecting means, an electron accelerating unit connected to the electron transmitting unit at one end and connected to the output connecting means at the other end, a microwave power source connected to the electron accelerating unit via the microwave transferring means, a power supply and control system connected to the electron transmitting unit and the microwave power source, wherein the power supply and control system is connected to the superior power supply and control system and the output connecting means is connected to the input connecting means of the common target unit.

In addition, in the apparatus generating flattening x-rays radiation field of the disclosure, the plurality of electron accelerators are electron linear accelerators having the same structure, wherein the plurality of electron accelerators have a common power supply and control system, a microwave power source, a microwave power dispensing means and each of the plurality of electron accelerators further comprises an electron transmitting unit connected to the power supply and control system, an output connecting means connected to the input connecting means of the common target unit, an electron accelerating unit connected to the electron transmitting unit at one end and connected to the output connecting means at the other end, a microwave transferring means connected to the electron accelerating unit.

In addition, in the apparatus generating flattening x-rays radiation field of the disclosure, the energies of the plurality of electron accelerators are same.

In addition, in the apparatus generating flattening x-rays radiation field of the disclosure, the energies of the plurality of electron accelerators are different.

In addition, in the apparatus generating flattening x-rays radiation field of the disclosure, the plurality of electron accelerators are in the same plane.

In addition, in the apparatus generating flattening x-rays radiation field of the disclosure, the plurality of electron accelerators are not in the same plane.

The present application provides a method for generating flattening x-rays radiation field, characterized in that, high-energy electron beam currents from plurality of electron accelerators bombard the target of the common target unit in a predetermined included angle in pairs.

In addition, in the method for generating flattening x-rays radiation field of the disclosure, the energies of the plurality of electron accelerators are same.

In addition, in the method for generating flattening x-rays radiation field of the disclosure, the energies of the plurality of electron accelerators are different.

In addition, in the method for generating flattening x-rays radiation field of the disclosure, the plurality of electron accelerators are in one plane.

In addition, in the method for generating flattening x-rays radiation field of the disclosure, the plurality of electron accelerators are not in one plane.

The present application aims at providing an apparatus and a method for generating a flattening x-ray radiation field. In the method for generating flattening the x-ray radiation field of the present application, at least two electron accelerators generate x-ray radiation field synchronously and the target positions are made same. The center direction of the x-rays radiation field generated by each electron accelerator forms a certain included angle, the size of which is related to the energy of the electron accelerator. The flattening x-rays radiation field is obtained by superposing the multiple x-rays radiation fields with an angle. In the apparatus generating flattening x-ray radiation field of the present application, it includes at least two electron accelerators and common target unit which is composed of plurality of input connectors, a vacuum target chamber, a target, a cooling system, a vacuum system and a focusing system etc.

This disclosure mainly provides an apparatus generating a flattening x-ray radiation field. The flattening x-ray radiation field of larger angles range is generated by superposition. Compared with the blocking way, the intensity of the flattening x-ray radiation field is large, thus the x-rays imaging system or radiation therapeutic system enjoys fast speed and high efficiency. In addition, compared with the way of blocking, the flattening x-ray radiation field of a larger angles range may be generated. Therefore, the objects of larger size and volume could be inspected by the fluoroscopic imaging system or uniform treatment could be performed on larger areas by the radiation therapeutic system. In addition, without the blocking of x-rays, blurred target spots or artifact will not occur, thus the image resolution and the definition of the fluoroscopic imaging inspecting system could be enhanced and the number of the electron accelerators could be increased. Therefore, the flattening x-ray radiation field of larger intensity and wider angle range could be obtained improving the performance of the fluoroscopic imaging system or radiation therapeutic system further and broaden the scope of application.

DETAILED DESCRIPTION OF THE PREFERRED EMBODIMENTS

Figure 1:
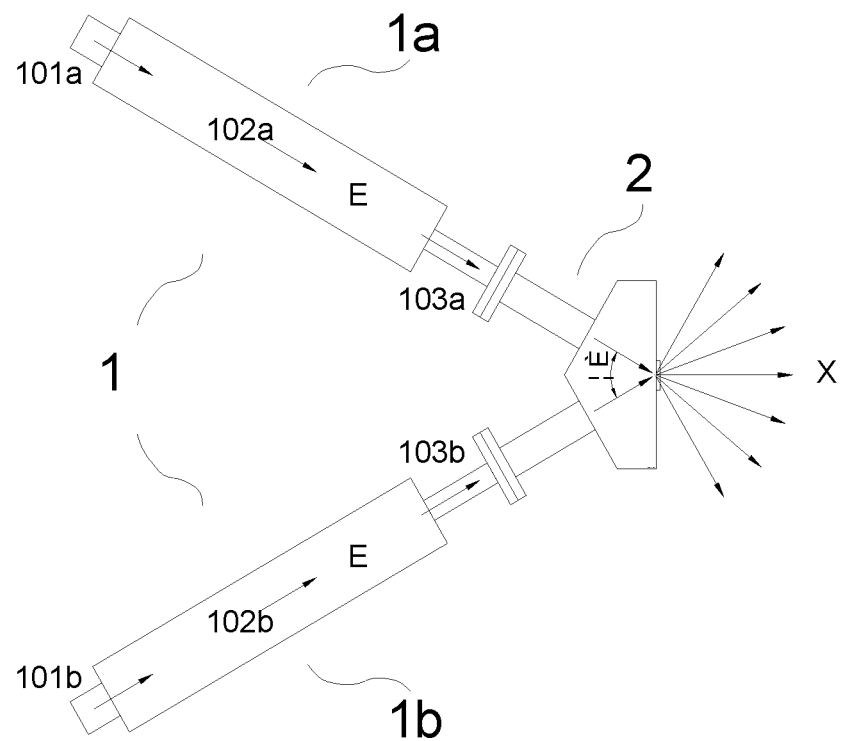
FIG. 1 is the schematic view of the apparatus generating flattening x-ray radiation field of the present application.
Figure 2:
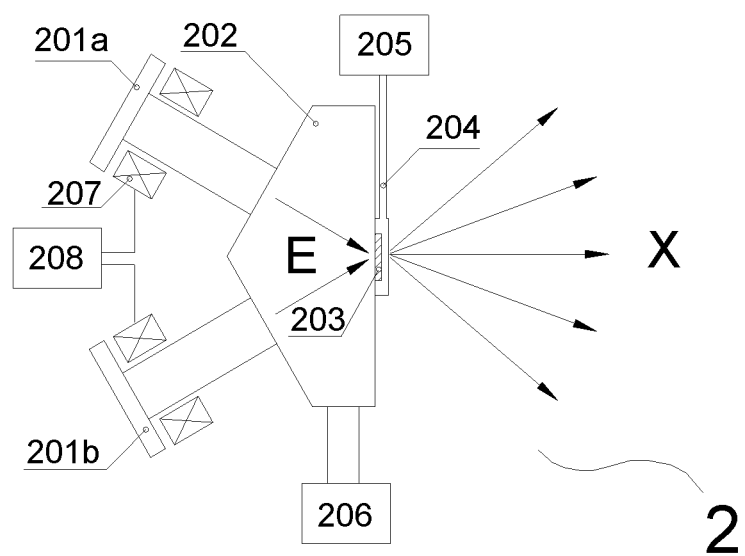
FIG. 2 is a schematic view of the structure of the common target unit of the present application.

Hereinafter, detailed description of the present disclosure will be given in combination with the accompanying drawings. FIG. 1 is a schematic view of the apparatus generating flattening x-ray radiation field of the present application. As shown in FIG. 1, the apparatus generating flattening x-ray radiation field is composed of plurality of electron accelerators 1 (at least two, specifically referred to as 1a, 1b) and a common target unit 2 connected to these electron accelerators 1a, 1b simultaneously. In addition, FIG. 2 is a schematic view of the structure of the common target unit of the present application. As shown in FIG. 2, the common target unit 2 is composed by a vacuum target chamber 202; plurality of input connectors 201 installed at one side of the vacuum target chamber 202 (in particular, input connecting means 201a, 201b); a target 203 installed on the vacuum target chamber 202 and located at the other side opposing the input connecting means 201.

In addition, as shown in FIG. 1, the electron accelerator 1 for generating high-energy electron beam current E typically includes electron transmitting units 101 (in particular 101a, 101b), electron accelerating units 102 (in particular 102a, 102b), output connecting means 103 (in particular 103a, 103b). The electron accelerator is a widely used device having various types, such as a high voltage accelerator, an inductive accelerator, a cyclotron, a linear accelerator etc. The rationale can be generalized as follows. Under the effect of the power supply and control system, the electron transmitting unit generates initial electron beam current which enters into the electron accelerator unit and is accelerated by the high voltage electric field or the inductive electric field or the microwave electric field thus obtaining high energy. The electron beam current then is output to various applications through output connecting means. In the present application, the output connecting means 103 of the electron accelerator 1 is connected to the input connecting means 201 of the common target unit 2. In addition, various conventional electron accelerators in the art can be used in the present application.

In addition, the common target unit 2 is used to aggregate multiple electron beam current E and make them bombard the same target in different directions so as to generate flattening x-rays. The common target unit 2 includes plurality of input connectors 201 (referred to as 201a, 201b etc respectively), a vacuum target chamber 202 and target 203. FIG. 2 shows the specific structure of the common target unit 2 in the present application. As shown in FIG. 2, plurality of input connectors 201 are installed at one side of the vacuum target chamber 202, and the target 203 is installed at the other side of the vacuum target chamber 202 opposing the input connecting means 201. The input connecting means 201 is typically composed of the knife edge flange and the pipe, normally in a circular shape. The circular knife edge flange is used to form a vacuum seal connection with the output connecting means 103 of the electron accelerator 1 and the circular pipe is used to make the electron beam current E pass therethrough. The axes of plurality of input connectors 201 intersect at one point at a predetermined included angle θ. The target 203 is located at the point of intersection that is typically the center of the target 203. The target 203 is fixed to the wall of the vacuum target chamber 202 which make the edge of the target 203, and the wall of vacuum target chamber 202 form a vacuum seal structure, e.g. by welding. The material of the target 203 is the heavy metal tungsten or tungsten alloy. The electron beam current E enters into the vacuum target chamber 202 from plurality of input connectors 201 and bombard the target 203 from different directions so as to generate flattening x-rays.

Figure 3:
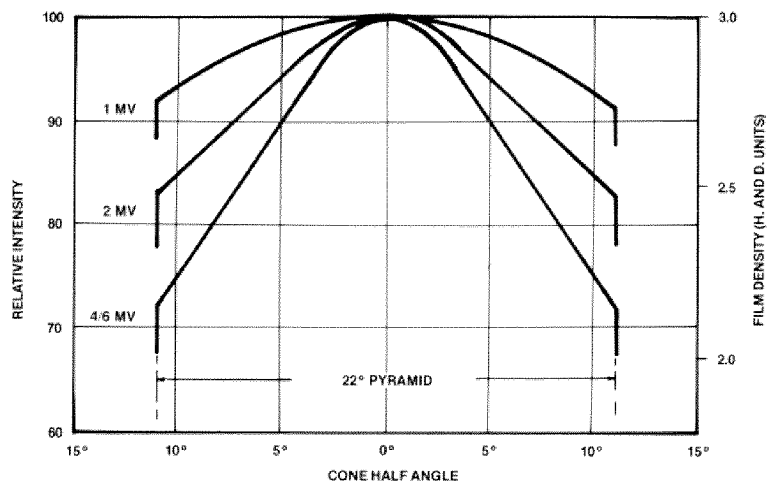
FIG. 3 is a schematic view of the intensity distribution of the x-rays generated by the electron accelerator of different energy in different directions.

In addition, FIG. 3 is a schematic view of the intensity distribution of the x-rays generated by a single electron accelerator of different energy in different directions. In FIG. 3, the horizontal axis represents angles, and 0 degree represents the moving direction of the electron beam current E, that is the center direction of the x-rays. Other angles demonstrate the deviating angle relative to the center direction. The vertical axis represents the relative intensity of the x-rays. Take the intensity of x-rays in the center direction as 100, and the intensity of the x-rays in other direction is the ratio relative to the center direction. FIG. 3 gives the intensity-angle distribution of the x-rays generated via bombarding the target by the electron beam current E which is generated by the electron accelerator of three kinds of different energy. As can be seen from the figure, the higher the energy is, the smaller the ratio of x-rays from other angles to that in the center direction is. In general, outside a certain range of angles, the x-rays cannot be used if the intensity drops too much. In other words, the more obvious the forward focusing effect of the x-rays is, the higher the energy of the accelerator is, and the smaller the angle range of the useful x-rays is. In the case that the difference of the intensity of x-rays in different directions is big, it affects the definition and luminance in different regions of an image in the fluoroscopic imaging inspection system. This leads to big difference of the therapeutic effect in different areas in the radiation therapeutic system. Therefore, as for the x-rays field generated by the electron accelerator with the energy above 6 MeV, if flattening is not performed, then the angle range that could be used effectively is very small.

Figure 4:
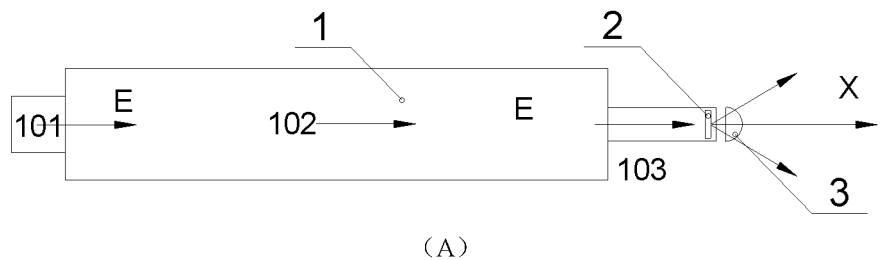
FIG. 4 is a schematic view of the conventional x-rays field flattening method, wherein (A) is a schematic view of the system architecture and (B) is the view showing the flattening effect.
Figure 4:
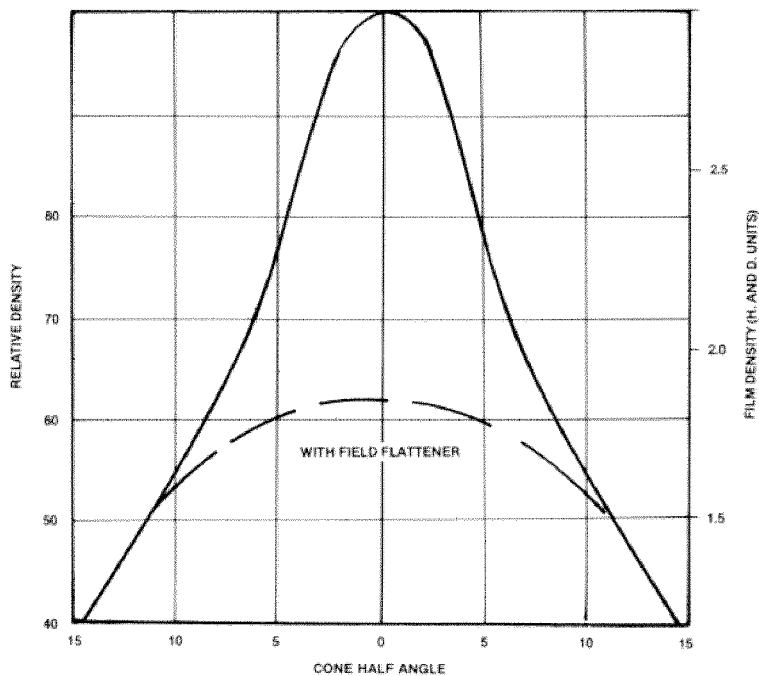

In addition, FIG. 4 is a schematic view of the conventional x-rays field flattening method. FIG. 4 (A) is a schematic view of the system architecture and FIG. 4 (B) is the view explaining the flattening effect. As shown in FIG. 4 (A), a flattening filter 3 is provided in front of the target of the electron accelerator. By the blocking of the flattening filter 3, the x-rays in the center direction weaken. Therefore, the flattening filter 3 is usually made of heavy metal tungsten with a shape of circular frustum like a small hill. That is, the center is the thickest giving the strongest block, and the margin becomes thinner giving less block. FIG. 4 (B) shows the distribution of the x-rays in various directions after being blocked by the flattening filter 3. In this figure, the solid line represents the intensity of the x-rays that has not been blocked while the dotted line represents the intensity of the x-rays that has been blocked. As can be seen from the figures, as for the x-rays generated by the electron accelerator of high energy (9 MeV in the embodiment of the figure), even if half of the intensity of the x-rays in the center direction is blocked, it can only ensure the uniformity in a smaller range of angles (in the embodiment of the figure, the range of ±10 degrees). This kind of flattening filter dramatically decreases the intensity of the x-ray sacrificing the efficiency.

Figure 5:
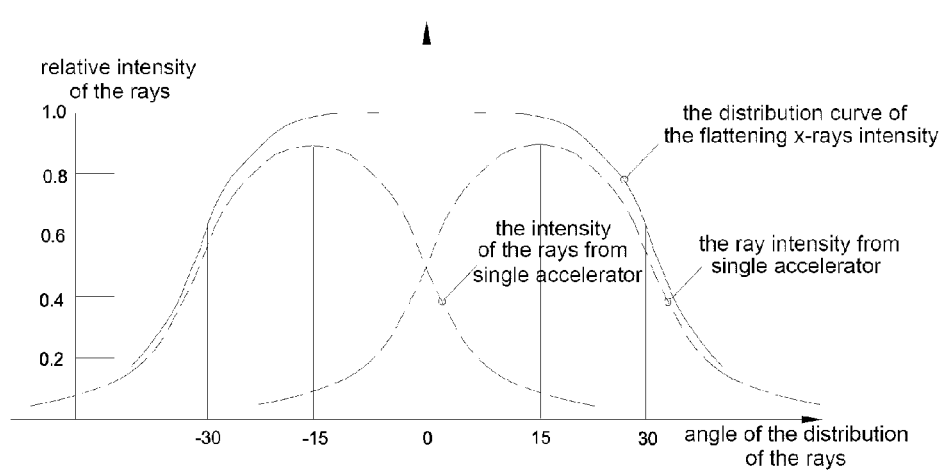
FIG. 5 is a schematic view of the flattening x-ray field generated by superposition of the two electron accelerators in the present application.

In addition, FIG. 5 is a schematic view of the flattening x-ray field generated by superposition of the two electron accelerators in the present application. The electron beam currents E generated by the two electron accelerators bombard the same target in a predetermined included angle θ. As shown in FIG. 5, the x-rays generated by each electron accelerator have some angle distribution. However, a flattening x-ray field with better evenness of the top in the new center direction taking the direction of the center of the included angle θ is formed after superposition of the x-rays fields generated by the two electron accelerators, namely the solid line in the figure. Compared with the x-rays field without superposition, the flattening x-ray field after superposition has an angle range of the useful x-rays more than doubled. More importantly, the area within the included angle θ of the direction of the forward motions of the two electron beam currents E forms an x-rays radiation field with the top in excellent evenness. This is much beneficiary to the image quality of the fluoroscopic imaging inspection system and the effect of the radiotherapy.

Certainly, to obtain a superposed x-rays field of remarkable uniform in a certain range of angles as shown in FIG. 5, the included angle of the electron beam current E depends not only on the distribution curve of the x-rays field of each electron accelerator, but also on the energy of the used electron accelerator. In accordance with the addition principle, it is easy to understand that the distribution curves of the two x-rays field of the two electron accelerators of definite energy are determined (referring to the dotted line in FIG. 5). When the included angle is the most preferable $\theta_0$, the x-rays field superposed in the area within the included angle θ in the direction of the forward motions of the two electron beam currents E has the best flatness (For example, the amplitude of fluctuation is less than ±5%. Actually it is very difficult to achieve totally flattening). When the included angle is larger than N, the directions of the two electron beam currents E deviate from the original center direction too much, thus the intensity of the superposed x-rays in the new center direction after superposition is not big enough, rendering the distribution curve of the superposed x-rays filed changed to "M" shape. Although the distribution of the useful angles becomes bigger, the uniformity is poorer (For example, the amplitude of fluctuation is larger than ±5%). It is disadvantageous that the negative effects exceed the positive effect. In addition, when the included angle is smaller than $\theta_0$, the directions of the two electron beam currents E deviate from the original center direction too little, thus the intensity of the superposed x-rays in the new center direction after superposition is too big, rendering the distribution curve of the superposed x-rays filed changed to "Λ" shape with the center portion too high (For example, the amplitude of fluctuation is larger than ±20%). The flattening in a range of larger angles has not been achieved, therefore, it requires an acceptable flattening distribution of the x-rays field (For example, the amplitude of fluctuation is larger than ±10%. The acceptable amplitude of fluctuation may be different depending on the different application fields). In addition, the beam current included angle θ of the electron beam currents E of the two electron accelerators has a corresponding relation with the energy En of the electron accelerator θ=θ(En), as shown in the relation curve in FIG. 6.

Figure 6:
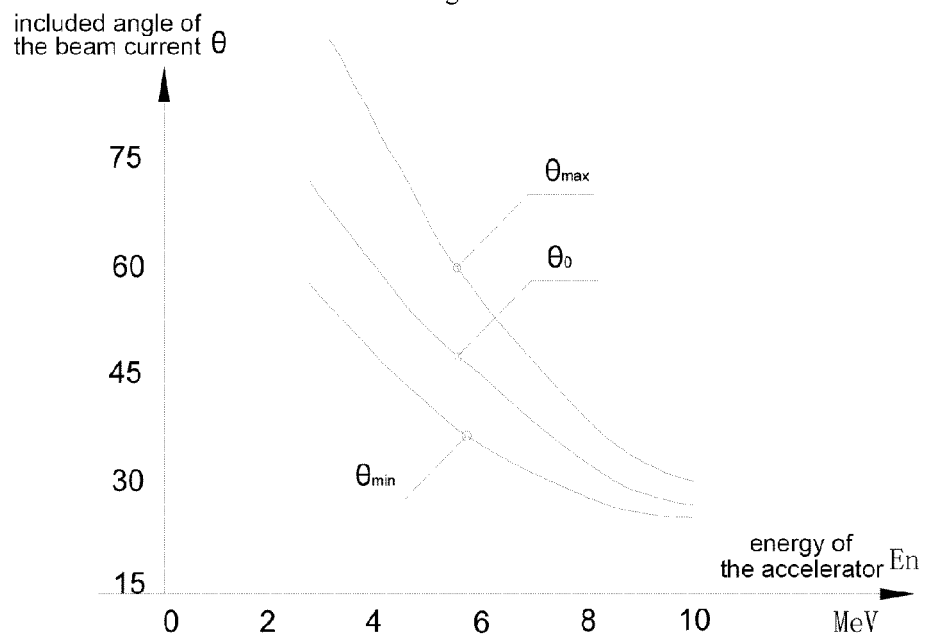
FIG. 6 is a schematic view of the relation of the included angle of the electron beam currents and the energy of the electron accelerator.

FIG. 6 shows the relation between the beam current included angle θ of the electron beam current E and the energy En of the electron accelerator in the present application. As shown in FIG. 6, when the included angle of the electron beam current E is $\theta_0$, the best flattening effect of the superposioned x-rays field could be obtained. $\theta_0$ decreases as the energy of the accelerator increases. In different application fields, there are some tolerance for the flattening effect of the superposed x-rays field, that is to say, the included angles of the electron beam current θ may shift up or down around $\theta_0$. Therefore, there are a maximum tolerance value $\theta_{max}$ and a minimum tolerance value $\theta_{min}$, both of which decrease as the energy of the electron accelerator increase. In addition, the higher the energy of the electron accelerator is, the smaller the fluctuation range of the $\theta_{max}$ and $\theta_{min}$ relative $\theta_0$ is.

In addition, in this disclose, it is preferable that the energy of the two electron accelerators are same, as shown in FIG. 5.

In addition, as shown in FIG. 2, the common target unit 2 in this disclosure further has a cooling means 204 and a refrigeration system 205. The cooling means 204 is installed outside the vacuum target chamber 202 enclosing a surface of the target 203. The interior is a pipe or a cavity through which the coolant is flowable inside the cooling means 204 so as to cool the target 203. Additionally, the refrigeration system 205 is connected to the cooling means 204. The refrigeration system 205 delivers the coolant of constant low temperature to the cooling means 204 and decreases the temperature of the high temperature coolant flowing back from the cooling means 204 to a predetermined value. When the high-energy electron beam current E bombards the target 203, a small portion of the energy converts to x-rays, and most energy converts into thermal energy. The temperature of the target 203 increases rapidly, and the coolant flowed circularly takes the heat away to keep the target 203 in a stable operating state. The refrigeration system 205 may be a common constant temperature water chilling unit or a constant temperature oil cooler. The coolant may be pure water, the antifreezing solution or the transformer oil etc.

In addition, as shown in FIG. 2, the common target unit 2 in this disclosure further has a vacuum system 206. The vacuum system 206 is installed on the side wall of the common target unit 2 and seal connected to the vacuum target chamber 202. The vacuum system 206 typically includes a vacuum pump, a vacuum pump power supply and a vacuum valve that is able to communicate with the outside. The vacuum valve is used to draw vacuum to the vacuum target chamber 202 by the exterior vacuum means after the common target unit 2 is seal connected to the electron accelerator 1. The vacuum pump is operated under the effect of the vacuum power supply so as to keep high vacuum during the operation of the vacuum target chamber 202.

In addition, as shown in FIG. 2, the common target 2 in this disclosure further includes a focusing means 207 and a focusing control means 208. The focusing means 207 are installed outside the input connecting means 201 and the number thereof is same as that of the input connecting means 201. The focusing control means 208 is connected to the focusing means 207 controlling the operating state of the focusing means 207. The focusing means 207 may be a focusing coil and the focusing control means 208 may be a focusing power supply. The operating state of the focusing control means 208 is controlled by the power supply and control system 107.

Figure 7:
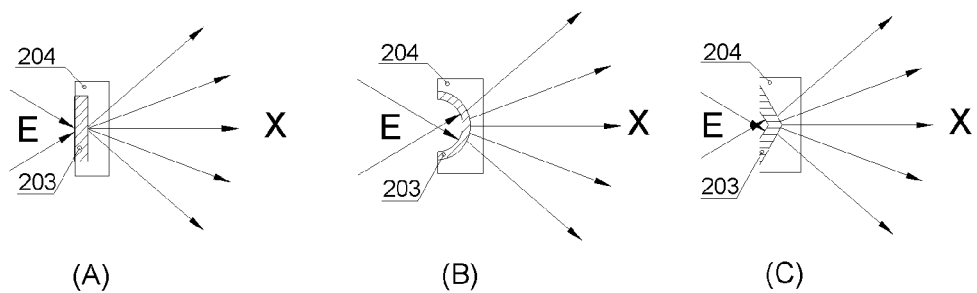
FIG. 7 is a schematic view of the structure of targets in different shapes in the present application.

FIG. 7 depicts the structures of the targets 203 in three different shapes.

As shown in FIG. 7(A), the target 203 of the common target unit 2 of the disclosure is a flat structure. In the case that the target 203 is a flat structure, the electron beam currents E entering into the vacuum target chamber 202 from various input commenting means 201 intersect at one point on the plane at the vacuum side. It is convenient to process the target 203 of a flat structure and the construction of the cooling means 204 is simple. However, the electron beam current E is incident on the plane of the target at an oblique angle.

In addition, as shown in FIG. 7 (B), the target 203 of the common target unit 2 in this disclosure is a spherical structure. In the case that the target 203 is a spherical structure, the electron beam currents E entering into the vacuum target chamber 202 from various input commenting means 201 intersect at the center of the spherical surface. Although the process of the target 203 in a spherical structure is more complex, the electron beam current E in each direction is incident to the plane of the target radically. The thickness of the target sensed by the electron beam current is uniform.

In addition, as shown in FIG. 7(C), the target 203 of the common target unit 2 in this disclosure is in a shape of L. That is, the target 203 is a structure of a flexed plane or a segmented plane. In the case that the target 203 is in a shape of L, it is maintained that the electron beam currents E entering into the vacuum target chamber 202 from various input connecting means 201 are all incident on the plane of the target vertically. The thickness of the target sensed by the electron beam current is also uniform.

Figure 8:
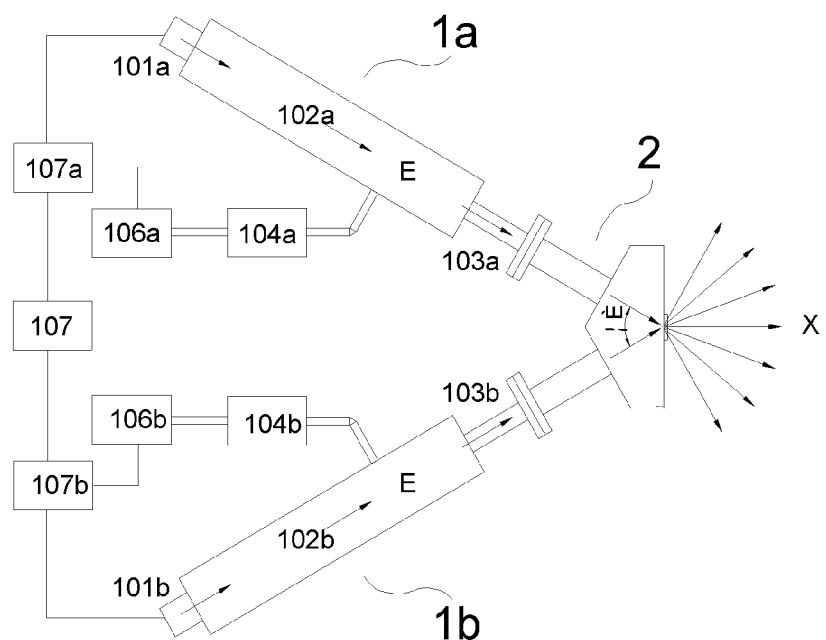
FIG. 8 depicts the apparatus generating flattening x-ray radiation field employing electron accelerator of independent structure in the present application.

FIG. 8 depicts a device generating a flattening x-ray radiation field by two electron linear accelerators with independent structures.

As shown in FIG. 8, the electron accelerator 1 in this disclosure is of high energy and small volume and good stability. The electron accelerator 1a and the electron accelerator 1b are independent to each other in the structure and are synchronous in the operating state, namely transmitting x-rays or stopping transmitting x-rays simultaneously under the control of superior power supply and control system 107. The electron accelerator 1a is composed of an electron transmitting unit 101a, an electron accelerating unit 102a, an output connecting means 103a, a microwave transferring means 104a, a microwave power source 106a, a power supply and control system 107a. The electron accelerator 1b is composed of an electron transmitting unit 101b, an electron accelerating unit 102b, an output connecting means 103b, a microwave transferring means 104b, a microwave power source 106b, a power supply and control system 107b. The power supply and control system 107a and the power supply and control system 107b are connected to the superior supply and control system 107. In addition, with regards to the structure of the electron accelerator 1a, the electron accelerating unit 102a is connected to the electron transmitting unit 101a at one end and connected to the output connecting means 103a at the other end. The power supply and control system 107a are connected to the electron transmitting unit 101a and the microwave power source 106a respectively. The microwave power source 106a is connected to the electron accelerating unit 102a via the microwave transferring means 104a. The structure of the electron accelerator 1b is same as that of the electron accelerator 1a. Under the effect of power supply and control system 107, the electron accelerator 1a and the electron accelerator 1b work simultaneously. The electron transmitting unit 101 generates initial electron beam current entering into the electron accelerating unit 102. At the same time, the microwave power source 106 generates the microwave power entering into the electron accelerating unit 102 via the microwave transferring means 104 and sets up a microwave accelerating electric field. The electron beam current E is effected under the microwave accelerating electric field in the electron accelerating unit 102 and accelerated obtaining high energy, and finally output to the common target unit 2 via the output connecting means 103.

Figure 9:
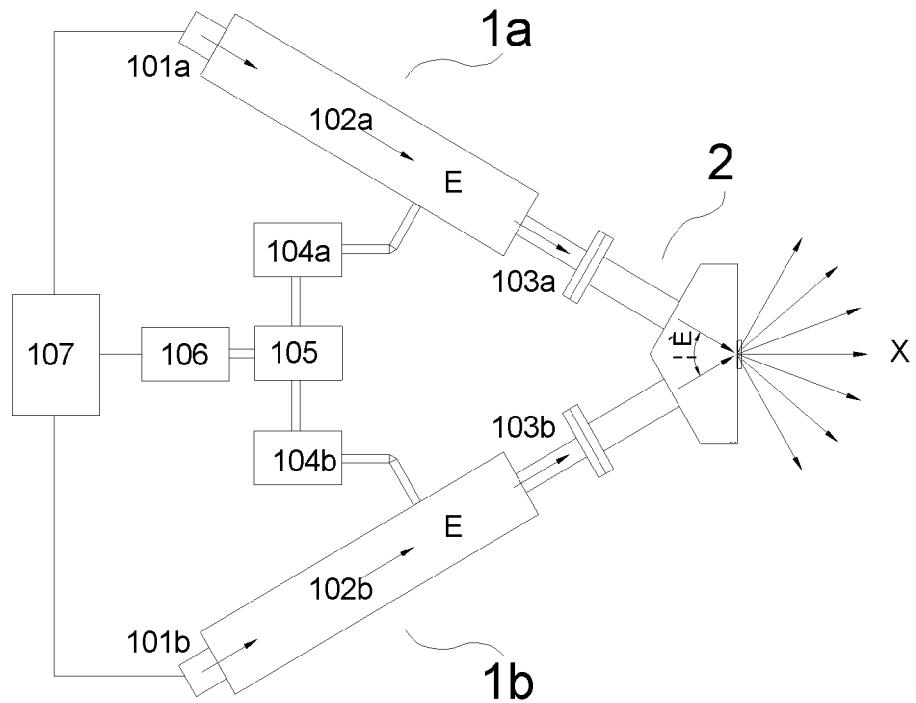
FIG. 9 depicts the apparatus generating flattening x-ray radiation field employing electron accelerator of non-independent structure in the present application.

In addition, FIG. 9 depicts the apparatus generating flattening x-ray radiation field employing the electron accelerator of non-independent structure in the present application.

As shown in FIG. 9, the electron accelerators 1a and 1b have a common power supply and control system 107, a microwave power source 106, and a microwave power dispensing means 105. Additionally, the electron accelerator 1a further includes electron transmitting unit 101a, the electron accelerating unit 102a, an output connecting means 103a, a microwave transferring means 104a, and the electron accelerator 1b further includes an electron transmitting unit 101b, an electron accelerating unit 102b, an output connecting means 103b, a microwave transferring means 104b. In addition, with regards to the structure of the electron accelerator 1a, the electron accelerator unit 102a is connected to the electron transmitting unit 101a at one end and connected to the output connecting means 103a at the other end. The electron transmitting unit 101a is connected to the power supply and control system 17 and the microwave transferring means 104a is connected to the electron accelerating unit 102a. The structure of the electron accelerator 1b is same as that of the electron accelerator 1a. Under the effect of the power supply and control system 107, the electron transmitting unit 101a and 101b simultaneously generate electron beam current entering into the electron accelerating unit 102a and 102b respectively. At the same time, the microwave power source 106 generates the microwave power that enters into the microwave power dispensing means 105 allocating into two portions uniformly. The two portions are output to two microwave transferring means 104a and 104b and are provided into the electron accelerating units 102a and 102b via the microwave transferring means 104a and 104b. The microwave electric fields are established in the electron accelerating units 102a and 102b simultaneously and the electron beam currents inside it are accelerated. The electron beam currents E are accelerated in the electron accelerating units 102a and 102b obtaining high energy and respectively enter into the common target unit 2 via the output connecting means 103a and 103b bombarding the target 203 at different angles, thus generating a flattening x-ray radiation field.

Figure 10:
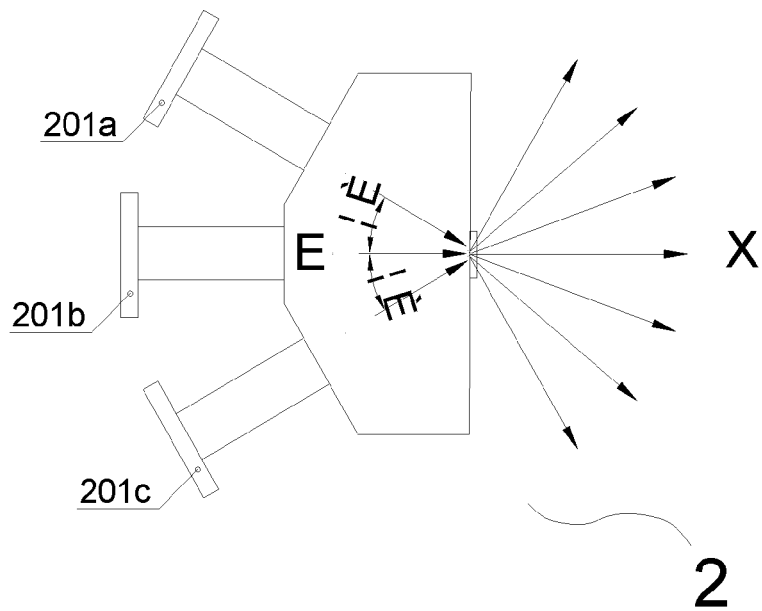
FIG. 10 is a schematic view of the structure of the common target unit which is capable of connecting three electron accelerators.

It should be specifically noted that the electron accelerators in the disclosure could be two or more. FIG. 10 depicts the structure of the common target unit 2 which is capable of connecting three electron accelerators. As shown in FIG. 10, the common target unit 2 has three input connecting means 201a, 201b, 201c that can be connected to the output connecting means of three electron accelerators respectively. The center lines of the three input connecting means 201a, 201b, 201c intersect at one point on the target 203. With regards to the two included angles composed by the two center lines adjacent to one another in the three center lines, preferably the two included angles are equal. This is because the higher the energy of the electron accelerator is, the more obvious the forward focusing of the x-rays generated by a single electron accelerator is. Even if it is superposed by two electron accelerators, the range of the angles of the obtained flattening x-ray radiation field is smaller. Therefore, when the energy of the accelerator is high (e.g. above 12 MeV) or the angle range of the flattening x-ray radiation field needs to be large, three or more electron accelerators needs to be connected to the common target unit 2 having more input connecting means as shown in FIG. 10 so as to generate the flattening x-ray radiation field of higher energy and larger angles range.

It should be specifically noted that, when the number of the electron accelerators in the present application is three or more, plurality of electron accelerators could be located in one plane or not in one plane. Correspondingly, the center line of plurality of input connectors of the common target unit 2 could be in one plane or not in one plane. In the case that plurality of electron accelerators are not in one plane, the center lines of electron beam currents E of plurality of electron accelerator still intersect at one point. The center lines of the electron beam currents of every two electron accelerators constitute one plane. The superposition of the x-rays radiation field generated by these two electron accelerators on the plane still has the flattening effect as shown in FIG. 5. The center lines of the electron beam currents E of plurality of electron accelerators may combine in pairs to form various planes. A flattening effect is obtained on each plane and a three-dimensional flattening effect is obtained when these planes are taken together. That is, the flattening x-ray radiation field generated at this time by the plurality of electron accelerators is a flattening x-ray radiation field having better coherence of intensity in a three-dimensional angles range.

It should be specifically noted that the energy of the plurality of electron accelerators may be same or different.

It should be specifically noted that the included angles formed by the center lines of the plurality of input connectors of the common target unit 2 in pairs of this disclosure may be equal or not.

Embodiments

System Configuration

As shown in FIGS. 2, 5 and 9, the apparatus generating flattening x-ray radiation field of this disclosure is composed of two electron linear accelerators 1a, 1b of high energy (e.g. 6 MeV) and a common target unit 2. The electron linear accelerators 1a, 1b have common power supply and control system 107, a microwave power source 106, a microwave power dispensing means 105. In addition, the electron accelerator 1a further includes an electron transmitting unit 101a, an electron accelerating unit 102a, an output connecting means 103a, a microwave transferring means 104a and the electron accelerator 1b further includes an electron transmitting unit 101b, an electron accelerating unit 102b, an output connecting means 103b, a microwave transferring means 104b. The electron accelerating unit 102 is the main body of the electron accelerator 1 and the electron transmitting unit 101 is connected to the front end of the electron accelerating unit 102. The output connecting means 103 is connected to the tail end of the electron accelerating unit 102 and the microwave transferring means 104 is connected to the electron accelerating unit 102. The power supply and control system 107 is connected to the electron transmitting unit 101a, 101b of the accelerator 1a,1b and control the electron transmitting unit 101a, 101b. In addition, the power supply and control system 107 is connected to the microwave power source 106 and control the microwave power source 106. The output of the microwave power source 106 is connected to the input end of the microwave power dispensing means 105 and the two output ends of the microwave power dispensing means 105 are connected to the microwave transferring means 104a and 104b of the two electron accelerators 1a and 1b respectively. Common target unit 2 includes two input connecting means 201a and 201b, a vacuum target chamber 202, a target 203, a cooling means 204, a refrigeration system 205, a vacuum system 206, a focusing means 207, and a focusing control means 208. The input connecting means 201a and 201b are installed at one side of the vacuum target chamber 202 and the target 203 is installed at the other side of the vacuum target chamber 202 opposing the input connecting means 201a, 201b. The center lines of the input connecting means 201a and 201b intersect at one point on the target 203, typically the center point on the target 203. The vacuum system 206 is installed on the side surface of the vacuum target chamber 202 that is not interfere with the input connecting means 201a and 201b as well as the target 203. The input connecting means 201a, 201b, the target 203, the vacuum system 206 and the vacuum target chamber 202 all together constitute a vacuum seal structure. The cooling means 204 is installed outside the target 203 enclosing the surface of the target 203 at the antivacuum side. The refrigeration system 205 is connected to the cooling means 204. The focusing means 207 is installed outside the input connecting means, and the number thereof is same as that of the input connecting means. The focusing control means 208 is connected to the focusing means 207 and control the operating state of the focusing means 207. The output connecting means 103a and 103b of the two electron linear accelerators 1a and 1b are connected to the input connecting means 201a and 201b of the common target unit 2.

(Operating Principle)

Under the effect of the power supply and control system 107, the electron transmitting units 101a and 101b generate the electron beam current entering into the electron accelerating units 102a and 102b simultaneously. At the same time, the microwave power source 106 generates the microwave power under the control of the power supply and control system 107. The microwave entering into the microwave power dispensing means 105 is allocated into two portions uniformly. The two portions are output to the microwave transferring means 104a and 104b and are provided into the electron accelerating units 102a and 102b via the microwave transferring means 104a and 104b. The microwave electric fields are established simultaneously in the electron accelerating units 102a and 102b and accelerate the electron beam currents E entering into the interior of the electron accelerating units 102a and 102b which are generated by the electron transmitting units 101a and 101b. The electron beam currents E are accelerated in the electron accelerating units 102a and 102b obtaining high energy and then enter into the common target unit 2 via the output connecting means 103a and 103b respectively bombarding the target 203 at different angles, thus forming two x-rays radiation field respectively as shown by the dotted lines in FIG. 5. These two x-rays radiation fields generated simultaneously superposes, thus forming the flattening x-ray radiation field as shown by the solid lines in FIG. 5. The x-rays have an excellent coherence of the intensity in a larger angles range (e.g. −20 degrees to 20 degrees).

In addition, a high vacuum of the vacuum target chamber 202 is obtained by the vacuum means 206 and the high vacuum is kept during operation. The heat generated during bombarding the target 203 by the electron beam current E is taken away by the cooling means 204 and the refrigeration system 205 so as to keep the operating temperature stable. The focusing means 207 is actuated by the focusing control means 208. Therefore, the electron beam current E is focused when passing through the input connecting means 201, and thereby the beam diameter of the electron beam current E diminishes.

Applying the apparatus generating a flattening x-ray radiation field of the present application to the x-rays imaging inspection system, get the inspected objects x-rayed by the high-energy x-rays of coherent intensity in a large distribution range of angles. The imaging angle is big, and the inspected volume is large as well as the image quality is high.

Applying the apparatus generating a flattening x-ray radiation field of the present application to the radiation therapy, the radiation therapy is conducted by the high-energy x-rays of coherent intensity in a large distribution range of angles. The therapy is performed evenly and the therapeutic effect is excellent.

Advantageous Effects

This disclosure mainly provides an apparatus generating a flattening x-ray radiation field. The flattening x-ray radiation field of larger angles range is generated by superposition. Compared with the blocking way in the prior art, the intensity of the flattening x-ray radiation field is large, thus the x-rays imaging system or radiation therapeutic system enjoys a fast speed and a high efficiency. In addition, compared with the way of blocking, the flattening x-ray radiation field of a larger angles range may be generated. Therefore, the objects of larger size and volume could be inspected by the fluoroscopic imaging system or uniform treatment could be performed on larger areas by the radiation therapeutic system. In addition, without the blocking of x-rays, blurred target spots or artifact will not occur, thus the image resolution and the definition of the fluoroscopic imaging inspecting system could be enhanced and the number of the electron accelerators could be increased. Therefore, the flattening x-ray radiation field of larger intensity and wider angle range could be obtained improving the performance of the fluoroscopic imaging system or radiation therapeutic system further and broaden the scope of application.

Embodiments have been disclosed above for the purpose of illustration but are not limited thereto. It should be appreciated that various modifications and combination are possible without departing from the scope and spirit of the accompanying claims.

LIST OF REFERENCE NUMBERS 1, 1a, 1b electron accelerator
101, 101a, 101b electron transmitting unit
102, 102a, 102b electron accelerating unit
103, 103a, 103b output connecting means
104 microwave transferring means
105 microwave power dispensing means
106 microwave power source
107 power supply and control system
2 common target unit
201, 201a, 201b input connecting means
202 vacuum target chamber
203 target
204 cooling means
205 refrigeration system
206 vacuum system
207 focusing means
208 focusing control means
3 flattening filter
E electron beam current
X x-rays
θ included angle of the electron beam current

What is claimed is:

1. An apparatus for generating a flattening x-ray radiation field comprising:
   a plurality of electron accelerators configured to generate a high-energy electron beam current; and
   a common target unit comprising a vacuum target chamber, a target and a plurality of input connectors;
   wherein, the plurality of electron accelerators are connected to the plurality of input connectors, respectively.

2. The apparatus according to claim 1, wherein the plurality of input connectors are connected to one side of the vacuum target chamber and the target is installed at the other side of the vacuum target chamber opposing the plurality of input connectors, wherein the axes of the plurality of input connectors intersect in pairs at one point at a predetermined included angle.

3. The apparatus according to claim 2, wherein the predetermined included angles of the axes of the plurality of input connectors intersect in pairs are same.

4. The apparatus according to claim 2, wherein the predetermined included angles of the axes of the plurality of input connectors intersect in pairs are different.

5. The apparatus according to claim 1, wherein, the target is a flat structure and the electron beam current entering into the vacuum target chamber from the plurality of input connectors intersect at one point on the target at the plane of the vacuum side.

6. The apparatus according to claim 1, wherein the target is a spherical structure and the electron beam currents entering into the vacuum target chamber from plurality of input connectors intersect at the center of the spherical surface.

7. The apparatus according to claim 1, wherein the target is a structure of "L" shape and the electron beam current entering into the vacuum target chamber from the plurality of input connectors is incident on the target surface vertically.

8. The apparatus according to claim 1, wherein the common target unit further comprises: a cooling means installed outside the vacuum target chamber enclosing one surface of the target, the interior thereof is a pipe or a cavity through which the coolant is flowable inside the cooling means so as to cool the target; a refrigeration system connected to the cooling means delivering the coolant of constant low temperature to the cooling means and decrease the temperature of the high temperature coolant flowing back from the cooling means to a predetermined value.

9. The apparatus according to claim 1, wherein the common target unit further comprises: a vacuum system installed on the side wall of the common target unit and seal connected to the vacuum target chamber such that a high vacuum can be maintained in the vacuum target chamber during operation.

10. The apparatus according to claim 1, wherein the common target unit further comprises: plurality of focusing means installed outside the input connecting means; a focusing control means connected to the focusing means to control the operating state of the focusing means.

11. The apparatus according to claim 1, wherein the plurality of electron accelerators are electron linear accelerators having the same structure, wherein the electron accelerator is composed of an electron transmitting unit, an output connecting means, an electron accelerating unit connected to the electron transmitting unit at one end and connected to the output connecting means at the other end, a microwave power source connected to the electron accelerating unit via the microwave transferring means, a power supply and control system connected to the electron transmitting unit and the microwave power source, wherein the power supply and control system is connected to the superior power supply and control system and the output connecting means is connected to the input connecting means of the common target unit.

12. The apparatus according to claim 1, wherein the plurality of electron accelerators are electron linear accelerators having the same structure, wherein the plurality of electron accelerators have a common power supply and control system, a microwave power source, a microwave power dispensing means and each of the plurality of electron accelerators further comprises an electron transmitting unit connected to the power supply and control system, an output connecting means connected to the input connecting means of the common target unit, an electron accelerating unit connected to the electron transmitting unit at one end and connected to the output connecting means at the other end, a microwave transferring means connected to the electron accelerating unit.

13. The apparatus according to claim 1, wherein the energies of the plurality of electron accelerators are same.

14. The apparatus according to claim 1, wherein the energies of the plurality of electron accelerators are different.

15. The apparatus according to claim 1, wherein the plurality of electron accelerators are in the same plane.

16. The apparatus according to claim 1, wherein the plurality of electron accelerators are not in the same plane.

17. A method for generating a flattening x-ray radiation field, comprising
providing an apparatus according to claim 1;
generating the high-energy electron beam current from the plurality of electron accelerators; and
bombarding the target of the common target unit at the predetermined included angle in pairs.

18. The method according to claim 17, wherein the energies of the plurality of electron accelerators may be same or may be different.

19. The method according to claim 17, wherein the plurality of electron accelerators are in one plane or are not in one plane.

20. The method according to claim 18, wherein the plurality of electron accelerators are in one plane or are not in one plane.

* * * * *